United States Patent
Faig et al.

(10) Patent No.: US 10,449,133 B1
(45) Date of Patent: Oct. 22, 2019

(54) COSMETIC COMPOSITIONS COMPRISING ACETYL TRIFLUOROMETHYLPHENYL VALYLGLYCINE

(71) Applicant: L'OREAL, Paris (FR)

(72) Inventors: Jonathan James Faig, Sayreville, NJ (US); Zachary Maron, Jersey City, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/110,268

(22) Filed: Aug. 23, 2018

(51) Int. Cl.
- *A61K 8/34* (2006.01)
- *A61K 8/37* (2006.01)
- *A61Q 19/08* (2006.01)
- *A61K 8/44* (2006.01)
- *A61K 8/49* (2006.01)

(52) U.S. Cl.
CPC .............. *A61K 8/442* (2013.01); *A61K 8/34* (2013.01); *A61K 8/345* (2013.01); *A61K 8/37* (2013.01); *A61K 8/4973* (2013.01); *A61Q 19/08* (2013.01)

(58) Field of Classification Search
CPC .......... A61K 8/442; A61K 8/34; A61K 8/345; A61K 8/37; A61K 8/4973; A61Q 19/08
USPC ....................................................... 514/563
See application file for complete search history.

(56) References Cited

U.S. PATENT DOCUMENTS

| | | |
|---|---|---|
| 2003/0152600 A1 | 8/2003 | Dalko et al. |
| 2004/0137024 A1 | 7/2004 | Abriat et al. |
| 2005/0187197 A1 | 8/2005 | Dalko et al. |
| 2006/0211659 A9 | 9/2006 | Dalko et al. |
| 2007/0202203 A1 | 8/2007 | Amar |
| 2008/0293962 A1 | 11/2008 | Dalko et al. |
| 2010/0152156 A1 | 6/2010 | Dahlstrom et al. |
| 2011/0021438 A1 | 1/2011 | Dalko et al. |
| 2011/0028447 A1 | 2/2011 | Buchler et al. |
| 2015/0335560 A1* | 11/2015 | Bernard ............ A61K 8/37 424/401 |
| 2017/0067884 A1 | 3/2017 | Srivastava et al. |

OTHER PUBLICATIONS

Mintel Data Base; "Eye Cream Treatment," Feb. 2008, http://www.gnpd.com.

* cited by examiner

*Primary Examiner* — Yong L Chu
(74) *Attorney, Agent, or Firm* — Polsinelli PC

(57) ABSTRACT

The present disclosure relates to cosmetic compositions including surprisingly high amounts of trifluoromethylphenyl valylglycine, which provides a variety of beneficial properties to skin. The cosmetic compositions include: (a) about 1 wt. % to about 25 wt. % of acetyl trifluoromethylphenyl valylglycine; (b) about 2 to about 30 wt. % of two or more solubilizing solvents selected from ethoxydiglycol, dimethyl isosorbide, triethyl citrate, isopropyl lauryl sarcosinate, and propylene glycol; and (c) optionally, water; wherein all weight percentages are based on the total weight of the cosmetic composition.

20 Claims, No Drawings

COSMETIC COMPOSITIONS COMPRISING ACETYL TRIFLUOROMETHYLPHENYL VALYLGLYCINE

FIELD OF THE DISCLOSURE

The present disclosure relates to cosmetic compositions that include acetyl trifluoromethylphenyl valylglycine and to methods for solubilizing acetyl trifluoromethylphenyl valylglycine using synergistic blends of solubilizing solvents.

BACKGROUND

Skin acts as a natural barrier between internal and external environments and therefore plays an important role in vital biological functions such as protection against mechanical and chemical injury, microorganisms, and ultraviolet damage. The health and appearance of skin, however, can deteriorate due to environmental factors, genetic makeup, nutrition, and sun exposure. Consumers desire to slow the gaining of skin and reduce the effects of aging, especially in the face and around the eyes. Radiant and clear skin appears youthful and is a sign of good health and vitality.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively influence the skin, causing dryness, rash, and puffiness.

Skin is broadly described as having two major components, the dermis and the epidermis. The dermis provides the epidermis with a solid support that nourishes the epidermis. The dermis is formed mainly by fibroblasts and an extracellular matrix, which includes primarily collagen, elastin and a substance known as ground substance. The epidermis is a desquamating pluristratified epithelium that is about 100 µm thick. The outermost part of the epidermis is a cornified layer (or stratum corneum) made from keratinocytes at the terminal stage of their differentiation (known as corneocytes). The cornified layer is responsible for the barrier function of the epidermis and provides the first line of defense from external insult. It helps protect skin from damage from physical, chemical, and infectious injuries. The cornified layer also helps protect the body from water loss.

Due to the structure and function of the skin, it presents unique challenges to the development of cosmetic and/or pharmaceutical products. Products for treating skin include active compounds, but many active compounds present challenges, for example, challenges with respect to solubility, stability, and/or effectiveness. It is difficult to stabilize certain active agents so they remain active during the shelf life of a product. It is also difficult to ensure that certain active agents penetrate the outer cornified layer of the skin to provide their desired effect.

SUMMARY OF THE DISCLOSURE

The present disclosure relates to cosmetic compositions that incorporate surprisingly high amounts of acetyl trifluoromethylphenyl valylglycine. Acetyl trifluoromethylphenyl valylglycine is a unique anti-aging agent. Although it imparts a multitude of beneficial properties to skin, acetyl trifluoromethylphenyl valylglycine is difficult to solubilize and therefore difficult to formulate into stable cosmetic compositions. It tends to crystalize out of formulations. Currently, no known commercially available products exist that include acetyl trifluoromethylphenyl valylglycine at concentrations of 0.5 wt. % or higher. The inventors of the instant case, however, discovered unique blends of solubilizing solvents that effectively solubilize acetyl trifluoromethylphenyl valylglycine allowing it to be incorporated into products in surprisingly high amounts.

The effective solubilizing solvents include ethoxydiglycol, dimethyl isosorbide, triethyl citrate, isopropyl lauryl sarcosinate, and propylene glycol. Ethoxydiglycol is a particularly effective solubilizing solvent, even on its own, but it is desirable to limit the total amount of ethoxydiglycol in cosmetic compositions. The inventors discovered that combinations of the solubilizing solvents are surprisingly useful and effective because they interact synergistically with each other to solubilize high amounts acetyl trifluoromethylphenyl trifluoromethylphenyl valylglycine. The synergistic activity of the combinations reduces the total amount of solubilizing solvents needed to solubilize the surprisingly high amounts of acetyl trifluoromethylphenyl valylglycine.

The cosmetic compositions of the instant disclosure include:
  (a) about 1 wt. % to about 25 wt. % of acetyl trifluoromethylphenyl valylglycine;
  (b) about 2 to about 30 wt. % of two or more solubilizing solvents selected from ethoxydiglycol, dimethyl isosorbide, triethyl citrate, isopropyl lauryl sarcosinate, and propylene glycol; and
  (c) optionally, water;
    wherein all weight percentages are based on the total weight of the cosmetic composition.

In some instances, the cosmetic compositions do not include isopropyl lauryl sarcosinate and propylene glycol as the only two solubilizing solvents. The cosmetic compositions may also optionally include additional components. Non-limiting examples of additional components include water-soluble solvent(s) (water-soluble solvents that are different than the "solubilizing solvents"), fatty compound(s), thickening agent(s), further skin active agent(s), etc. A more detailed description of additional components that may optionally be included in (or excluded from) the cosmetic compositions is provided later in the section entitled, "Detailed Description of the Disclosure."

The cosmetic compositions are particularly useful in methods for treating the skin, for example, methods for improving the appearance of skin including the skin of the face and/or neck and/or around the eyes. In particular, the cosmetic compositions are useful in methods for reducing the appearance of fine lines of the skin; reducing the appearance of wrinkles of the skin; improving the tone of skin and/or improving the evenness of skin tone; improving skin softness and/or smoothness; and/or increasing the radiance, luminosity, and/or glow of the skin.

DETAILED DESCRIPTION OF THE DISCLOSURE

The cosmetic compositions of the instant disclosure include surprisingly high amounts of acetyl trifluoromethylphenyl valylglycine. Unique blends of solubilizing solvents effectively solubilize acetyl trifluoromethylphenyl valylglycine allowing it to be incorporated in high amounts into cosmetic products. Combinations of solubilizing solvents are particularly useful because they interact synergistically with each other to solubilize the acetyl trifluoromethylphenyl valylglycine, thereby reducing the total amount of solubilizing solvents needed in cosmetic compositions.

The cosmetic compositions include:
(a) about 1 wt. % to about 25 wt. % of acetyl trifluoromethylphenyl valylglycine;
(b) about 2 to about 30 wt. % of two or more solubilizing solvents selected from ethoxydiglycol, dimethyl isosorbide, triethyl citrate, isopropyl lauryl sarcosinate, and propylene glycol; and
(c) optionally, water;
wherein all weight percentages are based on the total weight of the cosmetic composition.

In some instances, the cosmetic compositions do not include isopropyl lauryl sarcosinate and propylene glycol as the only two solubilizing solvents.

The cosmetic compositions typically include about 1 wt. % or more of acetyl trifluoromethylphenyl valylglycine. In some cases, the total amount of acetyl trifluoromethylphenyl valylglycine in the cosmetic composition is about 1 wt. % to about 25 wt. %, about 1 wt. % to about 20 wt. %, about 1 wt. % to about 15 wt. %, about 1 wt. % to about 10 wt. %, about 1 wt. % to about 5 wt. %, about 1 wt. % to about 3 wt. %, or about 1 wt. % to about 2 wt. %, based on the total weight of the cosmetic composition.

The "solubilizing solvents" of the instant disclosure include ethoxydiglycol, dimethyl isosorbide, triethyl citrate, isopropyl lauryl sarcosinate, and propylene glycol. Water, in combination with the solubilizing solvents, can also contribute to the solubilizing of acetyl trifluoromethylphenyl valylglycine. Nonetheless, water is not referred to as a "solubilizing solvent" in the instant disclosure but is set forth individually because the cosmetic compositions of the instant disclosure may be anhydrous.

In some instances, the two or more solubilizing solvents include at least ethoxydiglycol. Likewise, in some cases the two or more solubilizing solvent s include ethoxydiglycol and dimethyl isosorbide; and optionally one or more additional solubilizing solvents selected from triethyl citrate, isopropyl lauryl sarcosinate, and propylene glycol. Furthermore, in some cases the cosmetic compositions include ethoxydiglycol, dimethyl isosorbide, and propylene glycol.

In certain embodiments, the cosmetic compositions include:
(a) about 1 wt. % to about 25 wt. % of acetyl trifluoromethylphenyl valylglycine;
(b-i) ethoxydiglycol;
(b-ii) dimethyl isosorbide, triethyl citrate, isopropyl lauryl sarcosinate, and/or propylene glycol; and
(c) optionally, water.

The amounts for each of the components in the above embodiment can be the amounts discussed throughout the instant disclosure. The cosmetic compositions may also optionally include additional components, such as water-soluble solvent(s) (water-soluble solvents that are different from the "solubilizing solvents"), fatty compound(s), thickening agent(s), further skin active agent(s), etc.

In certain embodiments, the cosmetic compositions include:
(a) about 1 wt. % to about 25 wt. % of acetyl trifluoromethylphenyl valylglycine;
(b-i) dimethyl isosorbide;
(b-ii) ethoxydiglycol, triethyl citrate, isopropyl lauryl sarcosinate, and/or propylene glycol; and
(c) optionally, water.

The amounts for each of the components in the above embodiment can be the amounts discussed throughout the instant disclosure. The cosmetic compositions may also optionally include additional components, such as water-soluble solvent(s) (water-soluble solvents that are different from the "solubilizing solvents"), fatty compound(s), thickening agent(s), further skin active agent(s), etc.

In certain embodiments, the cosmetic compositions include:
(a) about 1 wt. % to about 25 wt. % of acetyl trifluoromethylphenyl valylglycine;
(b-i) triethyl citrate;
(b-ii) ethoxydiglycol, dimethyl isosorbide, isopropyl lauryl sarcosinate, and/or propylene glycol; and
(c) optionally, water.

The amounts for each of the components in the above embodiment can be the amounts discussed throughout the instant disclosure. The cosmetic compositions may also optionally include additional components, such as water-soluble solvent(s) (water-soluble solvents that are different from the "solubilizing solvents"), fatty compound(s), thickening agent(s), further skin active agent(s), etc.

In certain embodiments, the cosmetic compositions include:
(a) about 1 wt. % to about 25 wt. % of acetyl trifluoromethylphenyl valylglycine;
(b-i) isopropyl lauryl sarcosinate;
(b-ii) ethoxydiglycol, dimethyl isosorbide, triethyl citrate, and/or propylene glycol; and
(c) optionally, water.

The amounts for each of the components in the above embodiment can be the amounts discussed throughout the instant disclosure. The cosmetic compositions may also optionally include additional components, such as water-soluble solvent(s) (water-soluble solvents that are different from the "solubilizing solvents"), fatty compound(s), thickening agent(s), further skin active agent(s), etc.

In certain embodiments, the cosmetic compositions include:
(a) about 1 wt. % to about 25 wt. % of acetyl trifluoromethylphenyl valylglycine;
(b-i) propylene glycol;
(b-ii) ethoxydiglycol, dimethyl isosorbide, triethyl citrate, and/or isopropyl lauryl sarcosinate; and
(c) optionally, water.

The amounts for each of the components in the above embodiment can be the amounts discussed throughout the instant disclosure. The cosmetic compositions may also optionally include additional components, such as water-soluble solvent(s) (water-soluble solvents that are different from the "solubilizing solvents"), fatty compound(s), thickening agent(s), further skin active agent(s), etc.

The total amount of solubilizing solvents that can be included in the cosmetic compositions of the instant disclosure (including in the embodiments set forth above) can vary but is typically about 2 wt. % to about 30 wt. %, based on the total weight of the cosmetic composition. In some cases the total amount of solubilizing solvents is about 2 wt. % to about 25 wt. %, about 2 wt. % to about 20 wt. %, about 2 wt. % to about 15 wt. %, about 2 wt. % to about 10 wt. %, about 2 wt. % to about 8 wt. %, about 3 wt. % to about 30 wt. %, about 3 wt. % to about 25 wt. %, about 3 wt. % to about 20 wt. %, about 3 wt. % to about 15 wt. %, about 3 wt. % to about 10 wt. %, or about 3 wt. % to about 8 wt. %, based on the total weight of the cosmetic composition.

The individual amount of each individual solubilizing agent can vary. For instance, the total amount of ethoxydiglycol, when present, may be about 0.1 wt. % to about 15 wt. %, about 0.1 wt. % to about 12 wt. %, about 0.1 wt. % to about 10 wt. %, about 0.1 wt. % to about 8 wt. %, about 0.1 wt. % to about 5 wt. %, about 0.1 wt. % to about 2.5 wt. %, about 1 wt. % to about 15 wt. %, about 1 wt. % to about 12 wt. %, about 1 wt. % to about 10 wt. %, about 1 wt. % to about 5 wt. %, or about 1 wt. % to about 2.5 wt. %, based on the total weight of the cosmetic composition.

The total amount of dimethyl isosorbide may be, when present, about 0.1 wt. % to about 15 wt. %, about 0.1 wt. % to about 12 wt. %, about 0.1 wt. % to about 10 wt. %, about 0.1 wt. % to about 8 wt. %, about 0.1 wt. % to about 5 wt. %, about 0.1 wt. % to about 2.5 wt. %, about 1 wt. % to about 15 wt. %, about 1 wt. % to about 12 wt. %, about 1 wt. % to about 10 wt. %, about 1 wt. % to about 5 wt. %, or about 1 wt. % to about 2.5 wt. %, based on the total weight of the cosmetic composition.

The total amount of triethyl citrate may be, when present, about 0.1 wt. % to about 15 wt. %, about 0.1 wt. % to about 12 wt. %, about 0.1 wt. % to about 10 wt. %, about 0.1 wt. % to about 8 wt. %, about 0.1 wt. % to about 5 wt. %, about 0.1 wt. % to about 2.5 wt. %, about 1 wt. % to about 15 wt. %, about 1 wt. % to about 12 wt. %, about 1 wt. % to about 10 wt. %, about 1 wt. % to about 5 wt. %, or about 1 wt. % to about 2.5 wt. %, based on the total weight of the cosmetic composition.

The total amount of isopropyl lauryl sarcosinate may be, when present, about 0.1 wt. % to about 15 wt. %, about 0.1 wt. % to about 12 wt. %, about 0.1 wt. % to about 10 wt. %, about 0.1 wt. % to about 8 wt. %, about 0.1 wt. % to about 5 wt. %, about 0.1 wt. % to about 2.5 wt. %, about 1 wt. % to about 15 wt. %, about 1 wt. % to about 12 wt. %, about 1 wt. % to about 10 wt. %, about 1 wt. % to about 5 wt. %, or about 1 wt. % to about 2.5 wt. %, based on the total weight of the cosmetic composition.

The total amount of propylene glycol may be, when present, about 0.1 wt. % to about 15 wt. %, about 0.1 wt. % to about 12 wt. %, about 0.1 wt. % to about 10 wt. %, about 0.1 wt. % to about 8 wt. %, about 0.1 wt. % to about 5 wt. %, about 0.1 wt. % to about 2.5 wt. %, about 1 wt. % to about 15 wt. %, about 1 wt. % to about 12 wt. %, about 1 wt. % to about 10 wt. %, about 1 wt. % to about 5 wt. %, or about 1 wt. % to about 2.5 wt. %, based on the total weight of the cosmetic composition.

The cosmetic compositions of the instant disclosure may be anhydrous or aqueous. When water is present, the total amount of water can vary. For example, the total amount of water may be about 1 wt. % to about 90 wt. %, based on the total weight of the cosmetic composition. In some cases, the total amount of water may be about 1 wt. % to about 80 wt. %, about 10 wt. % to about 90 wt. %, about 10 wt. % to about 80 wt. %, about 30 wt. % to about 90 wt. %, about 30 wt. % to about 80 wt. %, about 50 wt. % to about 90 wt. %, about 50 wt. % to about 80 wt. %, about 60 wt. % to about 90 wt. %, about 60 wt. % to about 80 wt. %, or about 60 wt. % to about 75 wt. %, based on the total weight of the cosmetic composition.

The ratio of each individual solubilizing solvent with respect to another solubilizing solvent in the cosmetic composition can vary but in some instances is about 1:5 to about 5:1, about 1:4 to about 4:1, or about 1:3 to about 3:1. For example, if a cosmetic composition includes two solubilizing solvents, the ratio of the first solubilizing solvent to the second solubilizing solvent may be about 1:5 to about 5:1, about 4:1 to about 1:4, or about 1:3 to about 3:1. Similarly, if the cosmetic composition include three solubilizing solvents, the ratio of the ratio of the first solubilizing solvent to the second solubilizing solvent may be about 1:5 to about 5:1, about 4:1 to about 1:4, or about 1:3 to about 3:1. The ratio of the ratio of the second solubilizing solvent to the third solubilizing solvent may be about 1:5 to about 5:1, about 4:1 to about 1:4, or about 1:3 to about 3:1. The ratio of the first solubilizing solvent to the third solubilizing solvent may be about 1:5 to about 5:1, about 4:1 to about 1:4, or about 1:3 to about 3:1.

In some instances, the individual amount of each solubilizing solvent and the amount of water, if present, in the cosmetic compositions is sufficient to form at least a 9% by weight of an acetyl trifluoromethylphenyl valylglycine solution, based on the total weight of the acetyl trifluoromethylphenyl valylglycine, the solubilizing solvents, and the water, if present.

Similarly, in some instances, the individual amount of each solubilizing solvent and the water, if present, in the cosmetic compositions is sufficient to form at least a 10% by weight, at least a 12% by weight, at least a 15% by weight, at least a 17% by weight, at least a 20% by weight, or at least a 24% by weight of an acetyl trifluoromethylphenyl valylglycine solution, based on the total weight of the acetyl trifluoromethylphenyl valylglycine, the solubilizing solvents, and the water, if present.

Additional non-limiting lists of components useful in the cosmetic compositions of the instant disclosure are provided below.

Water-Soluble Solvents

The cosmetic compositions may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_{1-30}$, $C_{1-15}$, $C_{1-10}$, or $C_{1-4}$ alcohols), organic solvents, polyols (polyhydric alcohols), glycols (e.g., butylene glycol, caprylyl glycol, etc.), and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some instances, the cosmetic compositions of the disclosure include one or more glycols and/or one or more alcohols, for example, one or more water-soluble solvents selected from the group consisting of butylene glycol, caprylyl glycol, propanediol, glycerin, and a mixture thereof.

The total amount of the one or more water-soluble solvents can vary but is typically about 1 to about 40 wt. %, based on the total weight of the cosmetic composition. In some cases, the total amount of the one or more water-soluble solvents is about 1 to about 35 wt. %, about 1 to about 30 wt. %, about 1 to about 25 wt. %, about 2 to about 40 wt. %, about 2 to about 35 wt. %, about 2 to about 30 wt. %, about 2 to about 25 wt. %, about 5 to about 40 wt. %, about 5 to about 35 wt. %, about 5 to about 30 wt. %, about 5 to about 25 wt. %, about 10 to about 40 wt. %, about 10 to about 35 wt. %, about 10 to about 30 wt. %, about 10 to about 25 wt. %, about 15 to about 40 wt. %, about 15 to about 35 wt. %, about 15 to about 30 wt. %, or about 15 to about 25 wt. %, based on the total weight of the cosmetic composition.

Non-Silicone Fatty Compounds

The cosmetic composition may include one or more non-silicone fatty compounds. The term "non-silicone fatty compound" means a fatty compound that does not containing any silicon atoms (Si). Non-limiting examples of non-silicone fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting examples of polyglycerol esters of fatty acids include those of the following formula:

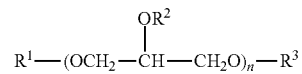

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Non-limiting examples of the high melting point compounds are found in the International Cosmetic Ingredient Dictionary, Sixteenth Edition, 2016, which is incorporated by reference herein in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distributions in which the main alkyl chain is cetyl, stearyl or behenyl groups. In the present application, more preferred fatty alcohols are cetyl alcohol, stearyl alcohol and mixtures thereof.

In some instances, the non-silicone fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a mixture thereof.

Mention may be made, among the waxes capable of being used as non-silicone fatty compounds, of animal waxes, such as beeswax; vegetable waxes, such as sunflower seed (*Helianthus annuus*), carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In some instance, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The total amount of non-silicone fatty compounds in the cosmetic compositions may vary, especially depending on whether the cosmetic composition is anhydrous or aqueous. Regardless of whether the cosmetic composition is anhydrous or aqueous, the total amount of fatty compounds may be about 5 to about 85 wt. %, based on the total weight of the cosmetic composition. In some cases, the total amount of the non-silicone fatty compounds. In some cases, regardless of whether the cosmetic composition is anhydrous or aqueous, the total amount of fatty compounds may be about 5 to about 80 wt. %, or about 5 to about 75 wt., based on the total weight of the cosmetic composition.

Cosmetic compositions that are anhydrous typically have a higher amount of total non-silicone fatty compounds. For instance, the total amount of non-silicone fatty compounds may be about 30 to about 85 wt. %, about 40 to about 85 wt. %, about 50 to about 85 wt. %, about 60 to about 85 wt. %, about 30 to about 80 wt. %, about 40 to about 80 wt. %, about 50 to about 80 wt. %, or about 60 to about 80 wt. %, based on the total weight of the cosmetic composition.

Cosmetic compositions that include water will often include lower amounts of total non-silicone fatty compounds. For instance, the total amount of non-silicone fatty compounds may be about 1 to about 60 wt. %, about 1 to about 50 wt. %, about 1 to about 40 wt. %, about 1 to about 30 wt. %, about 5 to about 60 wt. %, about 5 to about 50 wt. %, about 5 to about 40 wt. %, or about 5 to about 30 wt. %, based on the total weight of the cosmetic composition.

The cosmetic compositions are stable. The term "stable" as used herein means that the composition does not exhibit phase separation or visible crystallization after being subjected to 3 freeze/thaw cycles following by 2 months at 5° C., 25° C., and 45° C., wherein a freeze/thaw cycle is carried out by exposing the composition to freezing temperatures (approximately −15° C.±2° C.) for 24 hours and then subjecting the composition to room temperature (approximately 25° C.±2° C.) for 24 hours.

The cosmetic composition may be in any suitable physical form. Suitable forms include, but are not limited to emulsified or non-emulsified liquids, lotions, milks, mousses, sprays, gels, creams, pastes, and the like.

More exhaustive but non-limiting lists of components that may be included in (or excluded from) the cosmetic compositions of the instant disclosure are provided below.

Thickening Agents

The one or more thickening agents may be xanthan gum, guar gum, biosaccharide gum, cellulose, acacia Seneca gum, *sclerotium* gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the thickening agent includes ammonium polyacryloyldimethyl taurate and/or sodium polyacrylate.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerythritol. The carbomers are available as the CARBOPOL 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™ CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The total amount of thickening agent(s), when present, may vary but is typically about 0.01 to about 5 wt. %, based on the total weight of the cosmetic compositions. Similarly, the total amount of thickening agent(s) may be about 0.01 to about 4 wt. %, about 0.01 to about 3 wt. %, about 0.1 to about 5 wt. %, about 0.1 to about 4 wt. %, about 0.1 to about 3 wt. %, about 0.5 to about 5 wt. %, about 0.5 to about 4 wt. %, about 0.5 to about 3 wt. %, based on the total weight of the cosmetic composition.

Skin Active Ingredients

The cosmetic compositions described herein may include one or more skin active ingredients. Non-limiting examples skin active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases the skin active ingredient is adenosine.

In one embodiment, the cosmetic compositions include a skin active ingredient such as a humectant and moisturizing ingredients, an anti-aging agent, a depigmenting agent, an anti-wrinkle agent, or an agent that treats oily skin.

Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of *Imperata cylindra* sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract *Prophyridium cruentum* enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, *ferox*, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-O ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In one embodiment the cosmetic composition comprises a skin active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as *Cuivridone Solabia*—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea* ulmaria), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech;—extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of 'meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of cinchona bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20-phthalimidoperoxyhexanoic acid-citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

The cosmetic compositions may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more skin active ingredients. In some cases, the one or more skin active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

In certain embodiments, the cosmetic compositions include:
  (a) about 1 wt. % to about 25 wt. %, preferably about 1 to about 10 wt. %, more preferably about 1 to about 5 wt. % of acetyl trifluoromethylphenyl valylglycine;
  (b) about 2 to about 30 wt. %, preferably about 2 to about 15 wt. %, more preferably about 2 to about 10 wt. % of two or more solubilizing solvents selected from ethoxydiglycol, dimethyl isosorbide, triethyl citrate, isopropyl lauryl sarcosinate, and propylene glycol; and
  (c) optionally, water;
  (d) about 1 to about 40 wt. %, preferably about 5 to about 35 wt. %, more preferably about 10 to about 30 wt. % of one or more water soluble solvents, which are different than the solubilizing solvents of (b);

(e) one or more non-silicone fatty compounds, for example, about 5 to about 85 wt. %, preferably about 5 to about 80 wt. %, more preferably about 5 to about 75 wt. % of the one or more non-silicone fatty compounds;

wherein all weight percentages are based on the total weight of the cosmetic composition.

The cosmetic compositions of the above embodiment can be anhydrous or aqueous. If it is an aqueous cosmetic composition, it may optionally be in the form of an emulsion. In some instances, the cosmetic compositions do not include isopropyl lauryl sarcosinate and propylene glycol as the only two solubilizing solvents The ratio of each individual solubilizing solvent with respect to another solubilizing solvent in the cosmetic composition can vary but in some instances is about 1:5 to about 5:1, about 1:4 to about 4:1, or about 1:3 to about 3:1.

In some instances, the individual amount of each solubilizing solvent and the amount of water, if present, in the cosmetic compositions is sufficient to form at least a 9%, at least a 10%, at least a 12%, at least a 15%, at least a 17%, at least a 20%, or at least a 24% by weight of an acetyl trifluoromethylphenyl valylglycine solution, based on the total weight of the acetyl trifluoromethylphenyl valylglycine, the solubilizing solvents, and the water, if present.

Methods

The cosmetic compositions of the disclosure are particularly useful in methods for treating the skin, for example, methods for improving the appearance of skin including the skin of the face and/or neck and or around the eyes. In particular, the cosmetic compositions are useful in methods for reducing the appearance of fine lines of the skin; reducing the appearance of wrinkles of the skin; improving the tone of skin and/or improving the evenness of skin tone; improving skin softness and/or smoothness; and/or increasing the radiance, luminosity, and/or glow of the skin. Such methods typically entail topically applying a cosmetically effective amount of the cosmetic composition to the skin, for example, the skin of the face and/or the neck and/or around the eyes. The methods may include one application or multiple applications. For instance, the cosmetic compositions may be applied to the skin (e.g., the face and/or neck) once per week, once every-other-day, once per day, twice per day, or more than twice per day; and the application(s) repeated for a period of time, for example, every-other-day for one or two weeks, every day one week, two weeks, one month, two months, three months, six months, one year, or longer. In some cases, the cosmetic composition is regularly applied to the skin once for an initial period of time followed by regular application for a subsequent second period of time, wherein the regular application during the initial period is less frequent than the regular application during the subsequent second period of time. This allows the skin to adjust gradually to the cosmetic composition. For example, the cosmetic composition may be applied to the skin every-other-day for an initial period of time (e.g., for one week) and subsequently applied to the skin every day for a subsequent second period of time (e.g., for one week, four weeks, eight weeks, or longer).

Implementation of the present disclosure is provided by way of the following examples. The examples serve to illustrate the technology without being limiting in nature.

Example 1

Solubility Studies 5 wt. % (1 gram) of acetyl trifluoromethylphenyl valylglycine was added to various combinations of solubilizing solvents. The combinations that did not solubilize 5 wt. % (1 gram) of acetyl trifluoromethylphenyl valylglycine were given a ranking of "1." The combinations that successfully solubilized 5 wt. % (1 gram) of acetyl trifluoromethylphenyl valylglycine were subjected to freeze/thaw stability analysis before additional acetyl trifluoromethylphenyl valylglycine was added to the combination.

Freeze-thaw cycle testing is a type of stability testing to determine whether a combination will remain stable. It entails subjecting the combinations to a series of extreme, rapid temperature changes. The freeze-thaw testing was conducted by exposing the combinations to freezing temperatures (approximately −15° C.±2° C.) for 24 hours. The combinations were then maintained at a higher temperature (approximately 25° C.±2° C.) for 24 hours. The process was repeated for three cycles. After three cycles, the combinations were visually analyzed for phase separation and crystallization of the acetyl trifluoromethylphenyl valylglycine.

If the combinations withstood freeze-thaw testing (that remained stable without any signs of crystallization), additional acetyl trifluoromethylphenyl valylglycine was added to the combinations and the freeze-thaw testing repeated until failure (until no more acetyl trifluoromethylphenyl valylglycine could be solubilized in the combination). Combinations that solubilized 5 wt. % (1 gram) of acetyl trifluoromethylphenyl valylglycine were given the ranking "2." Combinations that solubilized 9.5 wt. % (2 grams) were given the ranking "3." Combinations that solubilized 17.4% (4 grams) were giving the ranking "4." Combinations that solubilized 24% (6 grams) of acetyl trifluoromethylphenyl valylglycine were given the ranking "5." The combination that solubilized more than 24% (more than 6 grams) was given the designation "6." The table below presents the results.

| # | Ethoxydiglycol (g) | Dimethyl Isosorbide (g) | Triethyl Citrate (g) | Isopropyl Lauryl Sarcosinate (g) | Propylene Glycol (g) | ER2947 (g) | ATV* (g) | Max Conc. | Rating |
|---|---|---|---|---|---|---|---|---|---|
| 1 | 7.5 | 7.5 | 0 | 0 | 3.75 | >6 | 0.25 | >24% | 6 |
| 2 | 3.75 | 11.25 | 0 | 0 | 0 | 6 | 4 | 24% | 5 |
| 3 | 11.25 | 3.75 | 0 | 0 | 0 | 6 | 4 | 24% | 5 |
| 4 | 7.5 | 7.5 | 0 | 0 | 0 | 6 | 4 | 24% | 5 |
| 5 | 15 | 0 | 0 | 0 | 0 | 6 | 4 | 24% | 5 |
| 6 | 0 | 7.5 | 0 | 3.75 | 7.5 | 4 | 0.25 | 17.40% | 4 |
| 7 | 0 | 0 | 11.25 | 0 | 7.5 | 4 | 0.25 | 17.40% | 4 |
| 8 | 7.5 | 0 | 7.5 | 0 | 3.75 | 4 | 0.25 | 17.40% | 4 |
| 9 | 3.75 | 0 | 11.25 | 0 | 3.75 | 4 | 0.25 | 17.40% | 4 |
| 10 | 11.25 | 0 | 0 | 3.75 | 3.75 | 4 | 0.25 | 17.40% | 4 |
| 11 | 7.5 | 0 | 0 | 0 | 11.25 | 4 | 0.25 | 17.40% | 4 |
| 12 | 7.5 | 0 | 3.75 | 3.75 | 3.75 | 4 | 0.25 | 17.40% | 4 |

-continued

| # | Ethoxydiglycol (g) | Dimethyl Isosorbide (g) | Triethyl Citrate (g) | Isopropyl Lauryl Sarcosinate (g) | Propylene Glycol (g) | ER2947 (g) | ATV* (g) | Max Conc. | Rating |
|---|---|---|---|---|---|---|---|---|---|
| 13 | 11.25 | 0 | 0 | 0 | 3.75 | 4 | 4 | 17.40% | 4 |
| 14 | 11.25 | 0 | 0 | 0 | 3.75 | 4 | 4 | 17.40% | 4 |
| 15 | 3.75 | 3.75 | 0 | 3.75 | 7.5 | 4 | 0.25 | 17.40% | 4 |
| 16 | 7.5 | 3.75 | 0 | 3.75 | 3.75 | 4 | 0.25 | 17.40% | 4 |
| 17 | 11.25 | 3.75 | 0 | 3.75 | 0 | 4 | 0.25 | 17.40% | 4 |
| 18 | 7.5 | 0 | 0 | 3.75 | 7.5 | 4 | 0.25 | 17.40% | 4 |
| 19 | 3.75 | 7.5 | 0 | 0 | 3.75 | 4 | 4 | 17.40% | 4 |
| 20 | 7.5 | 3.75 | 0 | 0 | 3.75 | 4 | 4 | 17.40% | 4 |
| 21 | 3.75 | 0 | 11.25 | 0 | 3.75 | 4 | 0.25 | 17.40% | 4 |
| 22 | 7.5 | 11.25 | 0 | 0 | 0 | 4 | 0.25 | 17.40% | 4 |
| 23 | 0 | 3.75 | 3.75 | 0 | 11.25 | 4 | 0.25 | 17.40% | 4 |
| 24 | 3.75 | 7.5 | 3.75 | 0 | 0 | 4 | 4 | 17.40% | 4 |
| 25 | 3.75 | 7.5 | 3.75 | 0 | 3.75 | 4 | 0.25 | 17.40% | 4 |
| 26 | 0 | 0 | 11.25 | 0 | 7.5 | 4 | 0.25 | 17.40% | 4 |
| 27 | 3.75 | 0 | 3.75 | 0 | 11.25 | 4 | 0.25 | 17.40% | 4 |
| 28 | 11.25 | 0 | 0 | 0 | 7.5 | 4 | 0.25 | 17.40% | 4 |
| 29 | 11.25 | 0 | 3.75 | 0 | 0 | 4 | 4 | 17.40% | 4 |
| 30 | 11.25 | 7.5 | 0 | 0 | 0 | 4 | 0.25 | 17.40% | 4 |
| 31 | 11.25 | 0 | 0 | 7.5 | 0 | 4 | 0.25 | 17.40% | 4 |
| 32 | 0 | 0 | 7.5 | 11.25 | 0 | 2 | 0.25 | 9.50% | 3 |
| 33 | 0 | 7.5 | 3.75 | 7.5 | 0 | 2 | 0.25 | 9.50% | 3 |
| 34 | 0 | 0 | 3.75 | 0 | 15 | 2 | 0.25 | 9.50% | 3 |
| 35 | 0 | 0 | 11.25 | 7.5 | 0 | 2 | 0.25 | 9.50% | 3 |
| 36 | 0 | 0 | 3.75 | 0 | 11.25 | 2 | 4 | 9.50% | 3 |
| 37 | 0 | 3.75 | 11.25 | 3.75 | 0 | 2 | 0.25 | 9.50% | 3 |
| 38 | 3.75 | 0 | 3.75 | 7.5 | 3.75 | 2 | 0.25 | 9.50% | 3 |
| 39 | 0 | 0 | 7.5 | 7.5 | 3.75 | 2 | 0.25 | 9.50% | 3 |
| 40 | 0 | 0 | 0 | 7.5 | 11.25 | 2 | 0.25 | 9.50% | 3 |
| 41 | 7.5 | 0 | 0 | 11.25 | 0 | 2 | 0.25 | 9.50% | 3 |
| 42 | 3.75 | 0 | 11.25 | 3.75 | 0 | 2 | 0.25 | 9.50% | 3 |
| 43 | 7.5 | 0 | 3.75 | 0 | 0 | 2 | 7.75 | 9.50% | 3 |
| 44 | 0 | 0 | 3.75 | 0 | 11.25 | 2 | 4 | 9.50% | 3 |
| 45 | 3.75 | 3.75 | 0 | 11.25 | 0 | 2 | 0.25 | 9.50% | 3 |
| 46 | 0 | 11.25 | 0 | 7.5 | 0 | 2 | 0.25 | 9.50% | 3 |
| 47 | 0 | 3.75 | 0 | 0 | 11.25 | 2 | 4 | 9.50% | 3 |
| 48 | 0 | 3.75 | 11.25 | 0 | 3.75 | 2 | 0.25 | 9.50% | 3 |
| 49 | 3.75 | 3.75 | 11.25 | 0 | 0 | 2 | 0.25 | 9.50% | 3 |
| 50 | 3.75 | 0 | 15 | 0 | 0 | 2 | 0.25 | 9.50% | 3 |
| 51 | 3.75 | 3.75 | 0 | 0 | 7.5 | 2 | 4 | 9.50% | 3 |
| 52 | 0 | 0 | 3.75 | 0 | 11.25 | 2 | 4 | 9.50% | 3 |
| 53 | 0 | 11.25 | 7.5 | 0 | 0 | 2 | 0.25 | 9.50% | 3 |
| 54 | 3.75 | 3.75 | 0 | 11.25 | 0 | 2 | 0.25 | 9.50% | 3 |
| 55 | 0 | 7.5 | 0 | 11.25 | 0 | 2 | 0.25 | 9.50% | 3 |
| 56 | 0 | 3.75 | 11.25 | 3.75 | 0 | 2 | 0.25 | 9.50% | 3 |
| 57 | 7.5 | 3.75 | 7.5 | 0 | 0 | 2 | 0.25 | 9.50% | 3 |
| 58 | 3.75 | 0 | 7.5 | 7.5 | 0 | 2 | 0.25 | 9.50% | 3 |
| 59 | 3.75 | 0 | 11.25 | 3.75 | 0 | 2 | 0.25 | 9.50% | 3 |
| 60 | 0 | 3.75 | 7.5 | 0 | 3.75 | 1 | 4 | 5% | 2 |
| 61 | 0 | 0 | 0 | 15 | 3.75 | 1 | 0.25 | 5% | 2 |
| 62 | 3.75 | 0 | 7.5 | 0 | 3.75 | 1 | 4 | 5% | 2 |
| 63 | 0 | 0 | 7.5 | 0 | 7.5 | 1 | 4 | 5% | 2 |
| 64 | 0 | 3.75 | 0 | 15 | 0 | 1 | 0.25 | 5% | 2 |
| 65 | 0 | 0 | 7.5 | 0 | 3.75 | 1 | 7.75 | >5% | 1 |
| 66 | 0 | 3.75 | 3.75 | 3.75 | 3.75 | 1 | 4 | >5% | 1 |
| 67 | 0 | 3.75 | 0 | 0 | 7.5 | 1 | 7.75 | >5% | 1 |
| 68 | 0 | 3.75 | 0 | 7.5 | 3.75 | 1 | 4 | >5% | 1 |
| 69 | 0 | 0 | 11.25 | 0 | 0 | 1 | 7.75 | >5% | 1 |
| 70 | 0 | 0 | 0 | 3.75 | 3.75 | 1 | 11.5 | >5% | 1 |
| 71 | 0 | 0 | 11.25 | 3.75 | 0 | 1 | 4 | >5% | 1 |
| 72 | 0 | 0 | 0 | 3.75 | 11.25 | 1 | 4 | >5% | 1 |
| 73 | 0 | 3.75 | 3.75 | 0 | 3.75 | 1 | 7.75 | >5% | 1 |
| 74 | 3.75 | 0 | 0 | 7.5 | 3.75 | 1 | 4 | >5% | 1 |
| 75 | 0 | 0 | 11.25 | 0 | 0 | 1 | 7.75 | >5% | 1 |
| 76 | 0 | 0 | 3.75 | 3.75 | 0 | 1 | 11.5 | >5% | 1 |
| 77 | 3.75 | 0 | 0 | 3.75 | 3.75 | 1 | 7.75 | >5% | 1 |
| 78 | 0 | 0 | 0 | 3.75 | 7.5 | 1 | 7.75 | >5% | 1 |
| 79 | 3.75 | 0 | 0 | 7.5 | 0 | 1 | 7.75 | >5% | 1 |
| 80 | 0 | 7.5 | 0 | 3.75 | 0 | 1 | 7.75 | >5% | 1 |
| 81 | 3.75 | 0 | 0 | 3.75 | 0 | 1 | 11.5 | >5% | 1 |
| 82 | 0 | 3.75 | 0 | 0 | 7.5 | 1 | 7.75 | >5% | 1 |
| 83 | 0 | 7.5 | 0 | 0 | 3.75 | 1 | 7.75 | >5% | 1 |
| 84 | 3.75 | 0 | 0 | 7.5 | 3.75 | 1 | 4 | >5% | 1 |
| 85 | 3.75 | 0 | 0 | 11.25 | 0 | 1 | 4 | >5% | 1 |
| 86 | 0 | 3.75 | 0 | 3.75 | 7.5 | 1 | 4 | >5% | 1 |

-continued

| # | Ethoxydiglycol (g) | Dimethyl Isosorbide (g) | Triethyl Citrate (g) | Isopropyl Lauryl Sarcosinate (g) | Propylene Glycol (g) | ER2947 (g) | ATV* (g) | Max Conc. | Rating |
|---|---|---|---|---|---|---|---|---|---|
| 87 | 0 | 7.5 | 7.5 | 0 | 0 | 1 | 4 | >5% | 1 |
| 88 | 0 | 7.5 | 3.75 | 0 | 0 | 1 | 7.75 | >5% | 1 |
| 89 | 0 | 0 | 7.5 | 7.5 | 0 | 1 | 4 | >5% | 1 |
| 90 | 3.75 | 0 | 0 | 0 | 0 | 1 | 15.25 | >5% | 1 |
| 91 | 3.75 | 3.75 | 3.75 | 3.75 | 0 | 1 | 4 | >5% | 1 |
| 92 | 0 | 7.5 | 0 | 0 | 0 | 1 | 11.5 | >5% | 1 |
| 93 | 0 | 0 | 0 | 7.5 | 0 | 1 | 11.5 | >5% | 1 |
| 94 | 0 | 7.5 | 3.75 | 3.75 | 0 | 1 | 4 | >5% | 1 |
| 95 | 3.75 | 0 | 0 | 3.75 | 0 | 1 | 11.5 | >5% | 1 |

*ATV = acetyl trifluoromethylphenyl valylglycine

Example 2

Cosmetic Compositions

The Combination 1 of Example 1, which solubilized more than 24 wt. % of acetyl trifluoromethylphenyl valylgycine, was used to formulate the cosmetic compositions in the table below. Composition A and Composition B include the synergistic blend of solubilizing solvents of Combination 1 of Example 1. Composition C is identical to Composition B except that it does not include the synergistic blend of solubilizing solvents. Composition A is an anhydrous balm. Compositions B and C are serums having a lotion-like consistency. Compositions B and C are oil-in-water emulsions.

| | INCI US | A | B | C |
|---|---|---|---|---|
| Active | ACETYL TRIFLUOROMETHYL-PHENYL VALYLGLYCINE | 1 | 1 | 1 |
| Solubilizing Solvents | ETHOXYDIGLYCOL | 2 | 2 | |
| | DIMETHYL ISOSORBIDE | 2 | 2 | |
| | PROPYLENE GLYCOL | 1 | 1 | |
| Water Soluble Solvents | BUTYLENE GLYCOL | | 8 | 8 |
| | CAPRYLYL GLYCOL | | 0.3 | 0.3 |
| | PROPANEDIOL | 3 | | |
| | GLYCERIN | 20 | 8 | 8 |
| Fatty Compounds | HYDROGENATED VEGETABLE OIL | 1.3 | | |
| | PRUNUS AMYGDALUS DULCIS (SWEET ALMOND) OIL | 2.5 | | |
| | HELIANTHUS ANNUUS (SUNFLOWER) SEED OIL | 20 | | |
| | PRUNUS ARMENIACA (APRICOT) KERNEL OIL | 7 | | |
| | BEESWAX | 2 | | |
| | C10-18 TRIGLYCERIDES | 10 | | |
| | GLYCERYL DIBEHENATE | 2.1 | | |
| | GLYCERYL BEHENATE | 0.7 | | |
| | TRIBEHENIN | 1.2 | | |
| | DICAPRYLYL CARBONATE | 3 | | |
| | CAPRYLIC/CAPRIC TRIGLYCERIDE | 17 | 5 | 5 |
| | ISONONYL ISONONANOATE | | 2 | 2 |
| | BUTYROSPERMUM PARKII (SHEA) BUTTER | | 1 | 1 |
| Thickening Agents | XANTHAN GUM | | 0.1 | 0.1 |
| | SODIUM POLYACRYLATE | | 1.8 | 1.8 |
| | ACRYLATES/BEHENETH-25 METHACRYLATE COPOLYMER | | 0.5 | 0.5 |
| Nonionic Emulsifiers/Surfactants | POLYGLYCERYL-3 METHYLGLUCOSE DISTEARATE | | 1.5 | 1.5 |
| | GLYCERYL STEARATE | 4 | | |
| Misc. Skin Actives | ADENOSINE | | 0.1 | 0.1 |
| | CAPRYLOYL SALICYLIC ACID | | 0.3 | 0.3 |
| Preservative | PRESERVATIVE, ANTIOXIDANT, CHELATING AGENTS, pH ADJUSTERS, FRAGRANCE, ETC. | ≤3 | ≤3 | ≤3 |
| | WATER | | 65 | 70 |

Composition A and Composition B, which both include the synergistic blend of solubilizing solvents, were stable. Composition C, however, which lacked solubilizing solvents, was not stable due to crystallization of the acetyl trifluoromethylphenyl valylglycine. Stability was determined using the freeze/thaw stability analysis described in Example 1.

The data show that the synergistic blend of solubilizing solvents solubilized the acetyl trifluoromethylphenyl valylglycine allowing it to be successfully incorporated into the cosmetic compositions in an amount of about 1 wt. %, which is higher than the amount present in any currently available commercial cosmetic product.

The data in Example 1 and Example 2 illustrate that, if desired, even higher amounts (higher than about 1 wt. %) of acetyl trifluoromethylphenyl valylglycine can be solubilized and incorporated into stable cosmetic compositions.

The foregoing description illustrates and describes the disclosure. The disclosure, however, shows and describes only the preferred embodiments. Nonetheless, it is to be understood that what is disclosed is capable of use in various other combinations, modifications, and environments and is capable of changes or modifications within the scope of the inventive concepts expressed herein, commensurate with the above teachings and/or the skill or knowledge of the relevant art. The embodiments described herein are provided to explain best modes for carrying out what is described and are provided to enable others skilled in the art to utilize the disclosure in such, or other, embodiments and with the various modifications required by the particular applications or uses thereof. Accordingly, the description is not intended to limit the inventive concepts to the forms or embodiments disclosed herein. Also, it is intended that the appended claims are construed as alternative embodiments.

As used herein, the terms "comprising," "having," and "including" (or "comprise," "have," and "include") are used in their open, non-limiting sense. The phrase "consisting of" is used in its closed sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

The term "a mixture thereof" is equivalent to the term "mixtures thereof." Throughout the disclosure, in situations where a list of alternatives is provided, the list of alternatives may include mixtures of the alternatives, even if not explicitly stated. In other words, the phase, "a mixture thereof," can be added to lists of elements provided throughout the disclosure. The phrase, "one or more elements selected from the group consisting of A, B, C, D, E, F, and a mixture thereof," does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions can be modified in all instances by the term "about," meaning within +/−5% of the indicated number.

Some of the various categories of components identified for the cosmetic compositions may overlap. In such cases where overlap may exist and the composition/product includes two overlapping components (or more than two overlapping components), an overlapping component does not represent more than one element of a claim. For example, a fatty acid may be defined as both a "fatty compound" and a "surfactant/emulsifier." If a claimed composition/product includes both a fatty compound and an emulsifier, a single fatty acid can serve as only a fatty compound or as only the surfactant/emulsifier (a single fatty acid does not serve as both the fatty compound and the surfactant/emulsifier).

All percentages, parts and ratios herein are based upon the total weight of the compositions, unless otherwise indicated.

The term "treat" (and its grammatical variations) as used herein refers to the application of the compositions of the present disclosure onto the surface of keratinous substrates such as the skin. The term 'treat," and its grammatical variations, relates to contacting skin with the cosmetic compositions of the present disclosure.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

All elements positively set forth in the instant disclosure can be negatively excluded, i.e., the compositions of methods can be "free," "substantially free," or "essentially free" of any of the elements positively set forth herein. The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.5 wt. %, or less than about 0.1 wt. %, or none of the specified material.

The term "anhydrous" as used herein means that the compositions is "substantially free" or "essentially free" of water, i.e., the composition contains less than about 2% by weight of a specific material added to a composition, based on the total weight of the compositions. Nonetheless, the compositions may include less than about 2 wt. % of water, based on the total weight of the cosmetic composition. Nonetheless, the cosmetic composition may contain less than about 1 wt. %, less than about 0.5 wt. %, less than about 0.5 wt. %, less than about 0.1 wt. %, or no water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
   (a) about 1 wt. % to about 25 wt. % of acetyl trifluoromethylphenyl valylglycine;
   (b) about 2 to about 30 wt. % of two or more solubilizing solvents selected from ethoxydiglycol, dimethyl isosorbide, triethyl citrate, isopropyl lauryl sarcosinate, and propylene glycol; and
   (c) optionally, water;
   wherein all weight percentages are based on the total weight of the cosmetic composition.

2. The cosmetic composition of claim 1 comprising:
   (a) about 1 wt. % to about 25 wt. % of acetyl trifluoromethylphenyl valylglycine;
   (b-i) about 1 to about 15 wt. % of ethoxydiglycol;
   (b-ii) about 1 to about 15 wt. % of dimethyl isosorbide, triethyl citrate, isopropyl lauryl sarcosinate, and/or propylene glycol; and
   (c) optionally, water.

3. The cosmetic composition of claim 1 comprising:
   (a) about 1 wt. % to about 25 wt. % of acetyl trifluoromethylphenyl valylglycine;
   (b-i) about 1 to about 10 wt. % of ethoxydiglycol;
   (b-ii) about 1 to about 10 wt. % of dimethyl isosorbide;
   (b-iii) about 1 to about 10 wt. % of triethyl citrate; and
   (c) optionally, water.

4. The cosmetic composition of claim 1 comprising:
   (a) about 1 wt. % to about 25 wt. % of acetyl trifluoromethylphenyl valylglycine;
   (b-i) about 1 to about 10 wt. % of ethoxydiglycol;
   (b-ii) about 1 to about 10 wt. % of dimethyl isosorbide;
   (b-iii) about 1 to about 10 wt. % of isopropyl lauryl sarcosinate; and
   (c) optionally, water.

5. The cosmetic composition of claim 1 comprising:
   (a) about 1 wt. % to about 25 wt. % of acetyl trifluoromethylphenyl valylglycine;
   (b-i) about 1 to about 10 wt. % of ethoxydiglycol;
   (b-ii) about 1 to about 10 wt. % of dimethyl isosorbide;
   (b-iii) about 1 to about 10 wt. % of propylene glycol; and
   (c) optionally, water.

6. The cosmetic composition of claim 2, wherein the weight ratio of the (b-i) ethoxydiglycol to the (b-ii) dimethyl isosorbide is about 1:4 to about 4:1.

7. The cosmetic composition of claim 1 comprising:
   (a) about 1 wt. % to about 25 wt. % of acetyl trifluoromethylphenyl valylglycine;
   (b-i) about 1 to about 15 wt. % of dimethyl isosorbide;
   (b-ii) about 1 to about 15 wt. % of ethoxydiglycol, triethyl citrate, isopropyl lauryl sarcosinate, and/or propylene glycol; and
   (c) optionally, water.

8. The cosmetic composition of claim 1 comprising:
(a) about 1 wt. % to about 25 wt. % of acetyl trifluoromethylphenyl valylglycine;
(b-i) about 1 to about 15 wt. % of triethyl citrate;
(b-ii) about 1 to about 15 wt. % of ethoxydiglycol, dimethyl isosorbide, isopropyl lauryl sarcosinate, and/or propylene glycol; and
(c) optionally, water.

9. The cosmetic composition of claim 1 comprising:
(a) about 1 wt. % to about 25 wt. % of acetyl trifluoromethylphenyl valylglycine;
(b-i) about 1 to about 15 wt. % of isopropyl lauryl sarcosinate;
(b-ii) about 1 to about 15 wt. % of ethoxydiglycol, dimethyl isosorbide, triethyl citrate, and/or propylene glycol; and
(c) optionally, water.

10. The cosmetic composition of claim 1 comprising:
(a) about 1 wt. % to about 25 wt. % of acetyl trifluoromethylphenyl valylglycine;
(b-i) about 1 to about 15 wt. % of propylene glycol;
(b-ii) about 1 to about 15 wt. % of ethoxydiglycol, dimethyl isosorbide, triethyl citrate, and/or isopropyl lauryl sarcosinate; and
(c) optionally, water.

11. The cosmetic composition of claim 1, further comprising:
(d) about 1 to about 40 wt. % of one or more water soluble solvents, which are different than the solubilizing solvents of (b).

12. The cosmetic composition of claim 1 that is essentially anhydrous and further comprises:
(e) about 40 to about 85 wt. % of one or more non-silicone fatty compounds.

13. The cosmetic composition of claim 1 comprising water and in the form of an emulsion, wherein the composition further comprises:
(e) about 1 to about 25 wt. % of one or more non-silicone fatty compounds.

14. The cosmetic composition of claim 1, further comprising:
(g) one or more thickening agents.

15. The cosmetic composition of claim 1, further comprising:
(f) about 1 to about 5 wt. % of one or more skin active agents.

16. The cosmetic composition of claim 1, wherein the cosmetic composition does not include isopropyl lauryl sarcosinate and propylene glycol as the only two solubilizing solvents.

17. The cosmetic composition of claim 1, wherein the individual amount of each solubilizing solvent and the water, if present, in the cosmetic compositions is sufficient to form at least a 9% by weight solution of acetyl trifluoromethylphenyl valylglycine, based on the total weight of the acetyl trifluoromethylphenyl valylglycine, the solubilizing solvents, and the water, if present.

18. A cosmetic composition comprising:
(a) about 1 wt. % to about 25 wt. % of acetyl trifluoromethylphenyl valylglycine;
(b) about 2 to about 30 wt. % of two or more solubilizing solvents selected from ethoxydiglycol, dimethyl isosorbide, triethyl citrate, isopropyl lauryl sarcosinate, and propylene glycol; and
(c) optionally, water;
(d) about 1 to about 40 wt. % of one or more water soluble solvents, which are different than the solubilizing solvents of (b);
(e) about 5 to about 85 wt. % of one or more non-silicone fatty compounds;
wherein all weight percentages are based on the total weight of the cosmetic composition.

19. A method for treating skin comprising applying a cosmetic composition of claim 1 to the skin.

20. A method for treating skin comprising applying a cosmetic composition of claim 18 to the skin.

* * * * *